United States Patent
Gericke et al.

(10) Patent No.: US 7,767,716 B2
(45) Date of Patent: Aug. 3, 2010

(54) ACYL HYDRAZINES AS KINASE INHIBITORS, IN PARTICULAR FOR SGK

(75) Inventors: Rolf Gericke, Seeheim-Jugenheim (DE); Dieter Dorsch, Ober-Ramstadt (DE); Werner Mederski, Zwingenberg (DE); Markus Klein, Weiterstadt (DE); Norbert Beier, Reinheim (DE); Florian Lang, Tuebingen (DE)

(73) Assignee: Merck Patent GmbH, Darmstadt (DE)

( * ) Notice: Subject to any disclaimer, the term of this patent is extended or adjusted under 35 U.S.C. 154(b) by 202 days.

(21) Appl. No.: 11/910,673

(22) PCT Filed: Mar. 10, 2006

(86) PCT No.: PCT/EP2006/002220

§ 371 (c)(1), (2), (4) Date: Oct. 4, 2007

(87) PCT Pub. No.: WO2006/105850

PCT Pub. Date: Oct. 12, 2006

(65) Prior Publication Data

US 2008/0167380 A1 Jul. 10, 2008

(30) Foreign Application Priority Data

Apr. 4, 2005 (DE) .................. 10 2005 015 255

(51) Int. Cl.
*C07C 243/38* (2006.01)
*A61K 31/166* (2006.01)

(52) U.S. Cl. ...................... 514/615; 564/150

(58) Field of Classification Search ............... None
See application file for complete search history.

(56) References Cited

U.S. PATENT DOCUMENTS 7,405,239 B2 * 7/2008 Gericke et al. ............. 514/546
7,619,115 B2 * 11/2009 Gericke et al. ............. 564/148
2005/0064501 A1 3/2005 Lang
2009/0221712 A1 * 9/2009 Gericke et al. ............. 514/615

FOREIGN PATENT DOCUMENTS

| JP | 2006-240189 | * | 9/2006 |
| WO | WO 00/62781 A | | 10/2000 |
| WO | WO 01/14412 A | | 3/2001 |

OTHER PUBLICATIONS

Vippagunta et al., Advanced Drug Delivery Reviews, 48, 3-26, 2001.*
Souillac, et al., Characterization of Delivery Systems, Differential Scanning Calorimetry in Encyclopedia of Controlled Drug Delivery, 1999, John Wiley & Sons, pp. 212-227.*
Golub et al., Science, vol. 286, Oct. 15, 1999, pp. 531-537.*
Machine Translation of JP 2006-240189, Sep. 14, 2006.*

* cited by examiner

*Primary Examiner*—Fiona T Powers
(74) *Attorney, Agent, or Firm*—Millen, White, Zelano, Branigan, P.C.

(57) ABSTRACT

Novel acyl hydrazides of the formula (I), in which $R^1$-$R^9$ have the meanings indicated in claim 1, are SGK inhibitors and can be used for the treatment of SGK-induced diseases and complaints, such as diabetes, obesity, metabolic syndrome (dyslipidaemia), systemic and pulmonary hypertonia, cardiovascular diseases and renal diseases, generally in fibroses and inflammatory processes of any type.

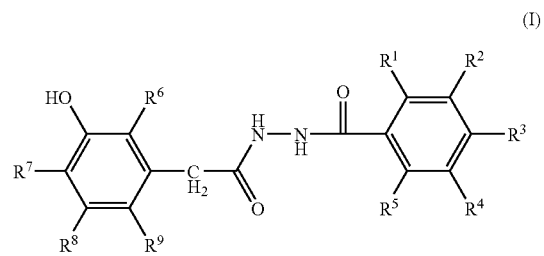

(I)

25 Claims, No Drawings

ACYL HYDRAZINES AS KINASE INHIBITORS, IN PARTICULAR FOR SGK

BACKGROUND OF THE INVENTION

The invention had the object of finding novel compounds having valuable properties, in particular those which can be used for the preparation of medicaments.

The present invention relates to compounds in which the inhibition, regulation and/or modulation of kinase signal transduction, in particular by the cell volume-regulated human kinase h-sgk (human serum and glucocorticoid dependent kinase or SGK), plays a role, furthermore to pharmaceutical compositions which comprise these compounds, and to the use of the compounds for the treatment of SGK-induced diseases.

The SGKs having the isoforms SGK-1, SGK-2 and SGK-3 are a serine/threonine protein kinase family (WO 02/17893).

The compounds according to the invention are preferably selective inhibitors of SGK-1. They may furthermore be inhibitors of SGK-2 and/or SGK-3.

In detail, the present invention relates to compounds which inhibit, regulate and/or modulate SGK signal transduction, to compositions which comprise these compounds, and to processes for the use thereof for the treatment of SGK-induced diseases and complaints, such as diabetes (for example diabetes mellitus, diabetic nephropathy, diabetic neuropathy, diabetic angiopathy and microangiopathy), obesity, metabolic syndrome (dyslipidaemia), systemic and pulmonary hypertonia, cardiovascular diseases (for example cardiac fibroses after myocardial infarction, cardiac hypertrophy and cardiac insufficiency, arteriosclerosis) and renal diseases (for example glomerulosclerosis, nephrosclerosis, nephritis, nephropathy, electrolyte excretion disorder), generally in fibroses and inflammatory processes of any type (for example liver cirrhosis, pulmonary fibrosis, fibrosing pancreatitis, rheumatism and arthroses, Crohn's disease, chronic bronchitis, radiation fibrosis, sclerormatitis, cystic fibrosis, scarring, Alzheimer's disease). The compounds according to the invention can also inhibit the growth of tumour cells and tumour metastases and are therefore suitable for tumour therapy.

The compounds according to the invention are furthermore used for the treatment of coagulopathies, such as, for example, dysfibrinogenaemia, hypoproconvertinaemia, haemophilia B, Stuart-Prower defect, prothrombin complex deficiency, consumption coagulopathy, hyperfibrinolysis, immunocoagulopathy or complex coagulopathies, and also in neuronal excitability, for example epilepsy. The compounds according to the invention can also be employed therapeutically in the treatment of glaucoma or a cataract. The compounds according to the invention are furthermore used in the treatment of bacterial infections and in antiinfection therapy. The compounds according to the invention can also be employed therapeutically for increasing learning ability and attention. In addition, the compounds according to the invention counter cell ageing and stress and thus increase life expectancy and fitness in the elderly.

The compounds according to the invention are furthermore used in the treatment of tinnitus.

The identification of small compounds which specifically inhibit, regulate and/or modulate SGK signal transduction is therefore desirable and an aim of the present invention.

It has been found that the compounds according to the invention and salts thereof have very valuable pharmacological properties while being well tolerated.

In particular, they exhibit SGK-inhibiting properties.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and also to a process for the treatment of the said diseases which comprises the administration of one or more compounds according to the invention to a patient in need of such an administration.

The host or patient may belong to any mammal species, for example a primate species, particularly humans; rodents, including mice, rats and hamsters; rabbits; horses, cows, dogs, cats, etc. Animal models are of interest for experimental investigations, where they provide a model for the treatment of a human disease.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-González, R. and Glenney, Jr., J. R. 1992, J. Biol. Chem. 267, page 14535).

Various assay systems are available for identification of kinase inhibitors. In the scintillation proximity assay (Sorg et al., J. of. Biomolecular Screening, 2002, 7, 11-19) and the flashplate assay, the radioactive phosphorylation of a protein or peptide as substrate using γATP is measured. In the presence of an inhibitory compound, a reduced radioactive signal, or none at all, is detectable. Furthermore, homogeneous time-resolved fluorescence resonance energy transfer (HTR-FRET) and fluorescence polarisation (FP) technologies are useful as assay methods (Sills et al., J. of Biomolecular Screening, 2002, 191-214).

Other non-radioactive ELISA assay methods use specific phospho anti-bodies (phospho ABs). The phospho AB only binds the phosphorylated substrate. This binding can be detected by chemoluminescence using a second peroxidase-conjugated antisheep antibody (Ross et al., Biochem. J., 2002, 366, 977-981).

PRIOR ART

WO 00/62781 describes the use of medicaments comprising inhibitors of cell volume-regulated human kinase H-SGK.

Benzylidenebenzohydrazides having an antibacterial action are described in WO 02/070464 A2. The use of acylhydrazides for the treatment of bacterial infections is disclosed in WO 01/70213.

Other acylhydrazone derivatives, inter alia for the treatment of diabetes complications, are disclosed in JP 11-106371.

Methoxy-substituted aromatic acylhydrazone derivatives for the treatment of cancer are described by T. Kametani et al. in Yakugaku Zasshi (1963), 83, 851-855 and in Yakugaku Zasshi (1963), 83, 844-847.

Other aromatic acylhydrazone derivatives as sedative enhancers and for lowering blood pressure are disclosed in JP 41-20699.

The use of kinase inhibitors in antiinfection therapy is described by C. Doerig in Cell. Mol. Biol. Lett. Vol. 8, No. 2A, 2003, 524-525.

The use of kinase inhibitors in obesity is described by N. Perrotti in J. Biol. Chem. 2001, Mar. 23; 276(12):9406-9412.

The following references suggest and/or describe the use of SGK inhibitors in disease treatment:

1: Chung E J, Sung Y K, Farooq M, Kim Y, Im S, Tak W Y, Hwang Y J, Kim Y I, Han H S, Kim J C, Kim M K. Gene expression profile analysis in human hepatocellular carcinoma by cDNA microarray. Mol Cells. 2002; 14:382-7.

2: Brickley D R, Mikosz C A, Hagan C R, Conzen S D. Ubiquitin modification of serum and glucocorticoid-induced protein kinase-1 (SGK-1). J Biol Chem. 2002; 277: 43064-70.

3: Fillon S, Klingel K, Warntges S, Sauter M, Gabrysch S, Pestel S, Tanneur V, Waldegger S, Zipfel A, Viebahn R, Haussinger D, Broer S, Kandolf R, Lang F. Expression of the serine/threonine kinase hSGK1 in chronic viral hepatitis. Cell Physiol Biochem. 2002; 12:47-54.

4: Brunet A, Park J, Tran H, Hu L S, Hemmings B A, Greenberg M E. Protein kinase SGK mediates survival signals by phosphorylating the forkhead transcription factor FKHRL1 (FOXO3a). Mol Cell Biol 2001; 21:952-65

5: Mikosz C A, Brickley D R, Sharkey M S, Moran T W, Conzen S D. Glucocorticoid receptor-mediated protection from apoptosis is associated with induction of the serine/threonine survival kinase gene, sgk-1. J Biol. Chem. 2001; 276:16649-54.

6: Zuo Z, Urban G, Scammell J G, Dean N M, McLean T K, Aragon I, Honkanen R E. Ser/Thr protein phosphatase type 5 (PP5) is a negative regulator of glucocorticoid receptor-mediated growth arrest. Biochemistry. 1999; 38:8849-57.

7: Buse P, Tran S H, Luther E, Phu P T, Aponte G W, Firestone G L. Cell cycle and hormonal control of nuclear-cytoplasmic localisation of the serum- and glucocorticoid-inducible protein kinase, Sgk, in mammary tumour cells. A novel convergence point of anti-proliferative and proliferative cell signalling pathways. J Biol. Chem. 1999; 274:7253-63.

8: M. Hertweck, C. Göbel, R. Baumeister: *C. elegans* SGK-1 is the critical component in the Akt/PKB Kinase complex to control stress response and life span. Developmental Cell, Vol. 6, 577-588, April, 2004.

SUMMARY OF THE INVENTION

The invention relates to compounds of the formula I

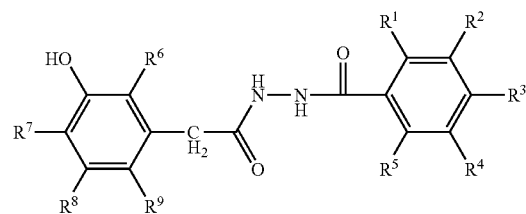

in which $R^1$, $R^2$, $R^3$, $R^4 R^5$, $R^6$, $R^7$, $R^8$, $R^9$ each, independently of one another, denote H, A, $OSO_2A$, Hal, $NO_2$, $OR^{10}$, $N(R^{10})_2$, CN, —$[C(R^{10})_2]_n$ $COOR^{10}$, O—$[C(R^{10})_2]_n COOR^{10}$, $SO_3H$, —$[C(R^{10})_2]_n$ Ar, —CO—Ar, O—$[C(R^{10})_2]_n$Ar, —$[C(R^{10})_2]_n$Het, —[C $(R^{10})_2]_n$C≡CH, O—$[C(R^{10})_2]_n$C≡CH, —$[C(R^{10})_2]_n$ $CON(R^{10})_2$, —$[C(R^{10})_2]_n CONR^{10}N(R^{10})_2$, O—[C $(R^{10})_2]_n CON(R^{10})_2$, O—$[C(R^{10})_2]_o CONR^{10}N(R^{10})_2$, $NR^{10}COA$, $NR^{10}CON(R^{10})_2$, $NR^{10}SO_2A$, $N(SO_2A)_2$, $COR^{10}$, $S(O)_m Ar$, $SO_2 NR^{10}$ or $S(O)_m A$, $R^1$ and $R^2$, $R^2$ and $R^3$, $R^3$ and $R^4$ or $R^4$ and $R^5$ together also denote CH=CH—CH=CH, A denotes unbranched or branched alkyl having 1-6 C atoms, in which 1-7H atoms may be replaced by F, or cyclic alkyl having 3-7 C atoms, Ar denotes phenyl, naphthyl or biphenyl, each of which is unsubstituted or mono-, di- or trisubstituted by Hal, A, $OR^{10}$, $N(R^{10})_2$, $NO_2$, CN, phenyl, $CON(R^{10})_2$, $NR^{10}COA$, $NR^{10}CON(R^{10})_2$, $NR^{10}SO_2A$, $COR^{10}$, $SO_2N(R^{10})_2$, $S(O)_m A$, —$[C(R^{10})_2]_n$—$COOR^{10}$ and/or —O[C $(R^{10})_2]_o$—$COOR^{10}$, Het denotes a mono- or bicyclic saturated, unsaturated or aromatic heterocycle having 1 to 4 N, O and/or S atoms, which may be mono-, di- or trisubstituted by Hal, A, $OR^{10}$, $N(R^{10})_2$, $NO_2$, CN, $COOR^{10}$, $CON(R^{10})_2$, $NR^{10}COA$, $NR^{10}SO_2A$, $COR^{10}$, $SO_2NR^{10}$, $S(O)_m A$, =S, =$NR^{10}$ and/or =O (carbonyl oxygen), $R^{10}$ denotes H or A, Hal denotes F, Cl, Br or I, m denotes 0, 1 or 2, n denotes 0, 1, 2 or 3, o denotes 1, 2 or 3, and pharmaceutically usable derivatives, salts, solvates and stereoisomers thereof, including mixtures thereof in all ratios.

The invention relates to the compounds of the formula I and salts thereof and to a process for the preparation of compounds of the formula I according to claims 1-16 and pharmaceutically usable derivatives, solvates, salts and stereoisomers thereof, characterised in that a) a compound of the formula II

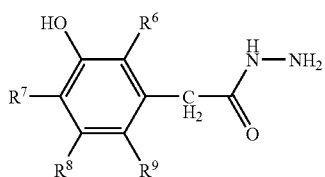

in which
R$^6$, R$^7$, R$^8$ and R$^9$ have the meanings indicated in claim 1,
is reacted with a compound of the formula III

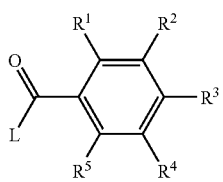

in which
L denotes Cl, Br, I or a free or reactively functionally modified OH group and
R$^1$, R$^2$, R$^3$, R$^4$ and R$^5$ have the meanings indicated in claim 1,
or
b) a compound of the formula IV

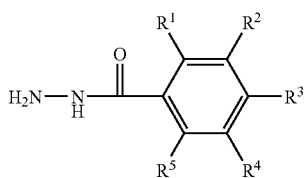

in which
R$^1$, R$^2$, R$^3$, R$^4$ and R$^5$ have the meanings indicated in claim 1,
is reacted with a compound of the formula V

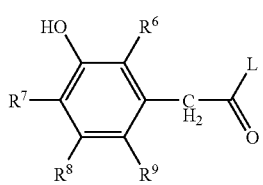

in which
L denotes Cl, Br, I or a free or reactively functionally modified OH group and
R$^6$, R$^7$, R$^8$ and R$^9$ have the meanings indicated in claim 1,
or
c) a radical R$^1$, R$^2$, R$^3$, R$^4$, R$^5$, R$^6$, R$^7$, R$^8$ and/or R$^9$ in a compound of the formula I is converted into another radical R$^1$, R$^2$, R$^3$, R$^4$, R$^5$, R$^6$, R$^7$, R$^8$ and/or R$^9$ by cleaving an ether by hydrolysis or hydrogenolysis, and/or a base or acid of the formula I is converted into one of its salts.

The invention also relates to the stereoisomers (E, Z isomers) and the hydrates and solvates of these compounds. Solvate of the compounds are taken to mean adductions of inert solvent molecules onto the compounds which form owing to their mutual attractive force. Solvate are, for example, mono- or dihydrates or alcoholates.

Pharmaceutically usable derivatives are taken to mean, for example, the salts of the compounds according to the invention and also so-called prodrug compounds.

Prodrug derivatives are taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as is described, for example, in Int. J. Pharm. 115, 61-67 (1995).

The expression "effective amount" means the amount of a medicament or pharmaceutical active ingredient which causes a biological or medical response which is sought or aimed at, for example by a researcher or physician, in a tissue, system, animal or human.

In addition, the expression "therapeutically effective amount" means an amount which, compared with a corresponding subject who has not received this amount, has the following consequence: improved treatment, healing, prevention or elimination of a disease, syndrome, condition, complaint, disorder or side effects or also the reduction in the progress of a disease, complaint or disorder.

The expression "therapeutically effective amount" also encompasses the amounts which are effective for increasing normal physiological function. The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

For all radicals which occur more than once, their meanings are independent of one another.

Above and below, the radicals and parameters R$^1$, R$^2$, R$^3$, R$^4$, R$^5$, R$^6$, R$^7$, R$^8$ and R$^9$ have the meanings indicated for the formula I, unless expressly indicated otherwise.

A denotes alkyl, is unbranched (linear) or branched, and has 1, 2, 3, 4, 5 or 6 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl. A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Ac denotes acetyl, Bn denotes benzyl, Ms denotes —SO$_2$CH$_3$.

R$^1$ preferably denotes H, A, Hal, NO$_2$, OR$^{10}$, —[C(R$^{10}$)$_2$]$_n$Ar or O—[C(R$^{10}$)$_2$]$_n$Ar, particularly preferably H, A, Hal, NO$_2$, OH, OCH$_3$, phenyl, benzyl, phenoxy or benzyloxy, very particularly preferably OH, Hal or A.

$R^2$ preferably denotes H, A, Hal, CN, $NO_2$, $OR^{10}$, —[C$(R^{10})_2]_n$Ar or O—[C$(R^{10})_2]_n$Ar, particularly preferably H, A, Hal, CN, $NH_2$, $NO_2$, OH, $OCH_3$, benzyl, phenyl, phenoxy or benzyloxy, very particularly preferably H, A or Hal.

$R^3$ preferably denotes H, A, Hal, $NO_2$, $OR^{10}$, —[C$(R^{10})_2]_n$Ar, O—[C$(R^{10})_2]_n$Ar, —[C$(R^{10})_2]_n$COOR$^{10}$ or S(O)$_m$A, particularly preferably H, A, Hal, $NO_2$, OH, $OCH_3$, phenyl, benzyl, phenoxy, benzyloxy, methoxycarbonyl, carboxyl or SA, very particularly preferably OH.

$R^4$ preferably denotes H, A, Hal, $CONH_2$, CN, $NO_2$ or $OR^{10}$, particularly preferably H, A, Hal, CN, $CONH_2$, $NO_2$, OH or $OCH_3$, very particularly preferably H.

$R^5$ preferably denotes H, A, Hal, $OR^{10}$, —[C$(R^{10})_2]_n$Ar or O—[C$(R^{10})_2]_n$Ar, particularly preferably H, A, Hal, OH, $OCH_3$, phenyl, benzyl, phenoxy or benzyloxy, particularly preferably H or OH.

$R^6$ preferably denotes H.

$R^7$ preferably denotes H or $OR^{10}$, particularly preferably H, OH or $OCH_3$, particularly preferably H.

$R^8$ preferably denotes H or $OR^{10}$, particularly preferably H, OH or $OCH_3$, very particularly preferably H.

$R^9$ preferably denotes H.

$R^{10}$ denotes H or A, preferably H or methyl. $R^{10}$ very particularly preferably denotes H.

Ar denotes, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)phenyl, o-, m- or p-(N,N-dimethylaminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methylsulfonyl)phenyl, o-, m- or p-cyanophenyl, o-, m- or p-ureidophenyl, o-, m- or p-formylphenyl, o-, m- or p-acetylphenyl, o-, m- or p-aminosulfonylphenyl, o-, m- or p-carboxyphenyl, o-, m- or p-carboxymethylphenyl, o-, m- or p-carboxymethoxyphenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar preferably denotes, for example, phenyl which is unsubstituted or mono-, di- or trisubstituted by Hal, A, $OR^{10}$, $SO_2$A, $COOR^{10}$ or CN, very particularly preferably phenyl which is unsubstituted or mono-, di- or trisubstituted by Hal and/or A.

Irrespective of further substitutions, Het denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 2-, 3-, 4-, 5-, 6- or 7-indazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated. Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, further preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl or 2,3-dihydro-2-oxofuranyl.

Het preferably denotes a monocyclic saturated, unsaturated or aromatic heterocycle having 1 to 2 N and/or O atoms, which may be unsubstituted or mono-, di- or trisubstituted by A, Hal, OH and/or OA.

Het particularly preferably denotes a monocyclic saturated heterocycle having 1 to 2 N and/or O atoms, which may be unsubstituted or mono- or disubstituted by A.

In a further embodiment, Het very particularly preferably denotes pyrrolidinyl, piperidinyl, morpholinyl or piperazinyl.

In a further embodiment, Het particularly preferably denotes furyl, thienyl, pyrrolyl, imidazolyl, pyridyl, pyrimidinyl, pyrazolyl, thiazolyl, indolyl, pyrrolidinyl, piperidinyl, morpholinyl or piperazinyl, each of which is unsubstituted or mono-, di- or trisubstituted by A, Hal, OH and/or OA.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Io, which conform to the formula I and in which the radicals not designated in greater detail have the meaning indicated for the formula I, but in which

| | | |
|---|---|---|
| in Ia | $R^1$ | denotes H, A, Hal, $NO_2$, $OR^{10}$, $—[C(R^{10})_2]_n Ar$ or $O—[C(R^{10})_2]_n Ar$; |
| in Ib | $R^2$ | denotes H, A, Hal, CN, $NO_2$, $OR^{10}$, $—[C(R^{10})_2]_n Ar$ or $O—[C(R^{10})_2]_n Ar$; |
| in Ic | $R^3$ | denotes H, A, Hal, $NO_2$, $OR^{10}$, $—[C(R^{10})_2]_n Ar$, $O—[C(R^{10})_2]_n Ar$, $—[C(R^{10})_2]_n COOR^{10}$ or $S(O)_m A$; |
| in Id | $R^4$ | denotes H, A, Hal, $CONH_2$, CN, $NO_2$ or $OR^{10}$; |
| in Ie | $R^5$ | denotes H, A, Hal, $OR^{10}$, $—[C(R^{10})_2]_n Ar$ or $O—[C(R^{10})_2]_n Ar$; |
| in If | $R^6$ | denotes H or A; |
| in Ig | $R^7$ | denotes H, A or $OR^{10}$; |
| in Ih | $R^8$ | denotes H, A or $OR^{10}$; |
| in Ii | $R^9$ | denotes H or A; |
| in Ij | Ar | denotes phenyl which is unsubstituted or mono-, di- or trisubstituted by Hal and/or A; |
| in Ik | Het | denotes a monocyclic saturated, unsaturated or aromatic heterocycle having 1 to 2 N and/or O atoms, which may be unsubstituted or mono-, di- or trisubstituted by A, Hal, OH and/or OA; |
| in Il | Het | denotes a monocyclic saturated heterocycle having 1 to 2 N and/or O atoms, which may be unsubstituted or mono- or disubstituted by A; |
| in Im | Het | denotes furyl, thienyl, pyrrolyl, imidazolyl, pyridyl, pyrimidinyl, pyrazolyl, thiazolyl, indolyl, pyrrolidinyl, piperidinyl, morpholinyl or piperazinyl, each of which is unsubstituted or mono-, di- or trisubstituted by A, Hal, OH and/or OA; |
| in In | $R^1$ | denotes H, A, Hal, $NO_2$, $OR^{10}$, $—[C(R^{10})_2]_n Ar$ or $O—[C(R^{10})_2]_n Ar$, |
| | $R^2$ | denotes H, A, Hal, CN, $N(R^{10})_2$, $NO_2$, $OR^{10}$, $—[C(R^{10})_2]_n Ar$ or $O—[C(R^{10})_2]_n Ar$, |
| | $R^3$ | denotes H, A, Hal, $NO_2$, $OR^{10}$, $—[C(R^{10})_2]_n Ar$, $O—[C(R^{10})_2]_n Ar$, $—[C(R^{10})_2]_n COOR^{10}$ or $S(O)_m A$, |
| | $R^4$ | denotes H, A, Hal, $CONH_2$, CN, $NO_2$ or $OR^{10}$, |
| | $R^5$ | denotes H, A, Hal, $OR^{10}$, $—[C(R^{10})_2]_n Ar$ or $O—[C(R^{10})_2]_n Ar$, |
| | $R^6$ | denotes H, |
| | $R^7$ | denotes H or $OR^{10}$, |
| | $R^8$ | denotes H or $OR^{10}$, |
| | $R^9$ | denotes H, |
| | $R^1$ and $R^2$, $R^2$ and $R^3$, $R^3$ and $R^4$ or $R^4$ and $R^5$ | together also denote CH=CH—CH=CH, |
| | A | denotes unbranched or branched alkyl having 1-6 C atoms, in which 1-7 H atoms may be replaced by F, |
| | Ar | denotes phenyl which is unsubstituted or mono-, di- or trisubstituted by Hal and/or A, |
| | $R^{10}$ | denotes H or A, |
| | Hal | denotes F, Cl, Br or I, |
| | m | denotes 0, 1 or 2, |
| | n | denotes 0, 1, 2 or 3; |
| in Io | $R^1$ | denotes OH, A or Hal, |
| | $R^2$ | denotes H, A or Hal, |
| | $R^3$ | denotes OH, |
| | $R^4$ | denotes H, A or Hal, |
| | $R^5$ | denotes H or OH, |
| | $R^6$ | denotes H, |
| | $R^7$ | denotes H, |
| | $R^8$ | denotes H, |
| | $R^9$ | denotes H, |
| | $R^1$ and $R^2$, $R^2$ and $R^3$, $R^3$ and $R^4$ or $R^4$ and $R^5$ | together also denote CH=CH—CH=CH, |
| | A | denotes unbranched or branched alkyl having 1-6 C atoms, in which 1-7 H atoms may be replaced by F, |
| | Hal | denotes F, Cl, Br or I; | and pharmaceutically usable derivatives, solvates, salts and stereoisomers thereof, including mixtures thereof in all ratios.
The compounds of the formula I are particularly preferably selected from the group
| No. | Structural formula | M.p. [° C.] |
|---|---|---|
| 1 | 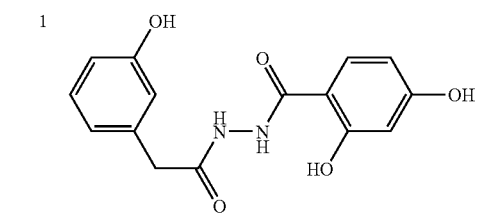 | 233-235 |
| 57 | 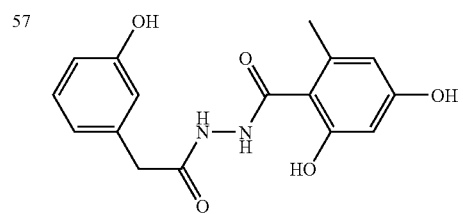 | 226-227 |
| 60 | 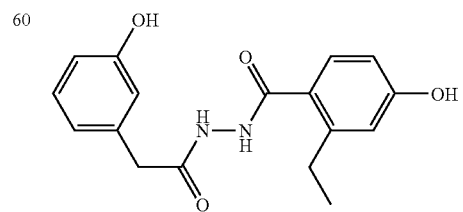 | 199-200 |
| 61 | 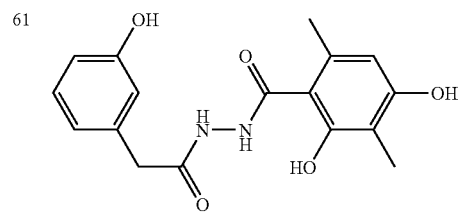 | 193-194 |
| 62 | 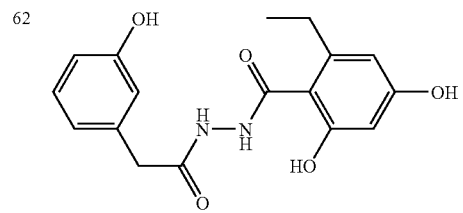 | 251 |
| 63 | 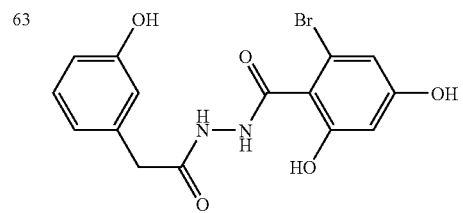 | 226-227 |
-continued
| No. | Structural formula | M.p. [° C.] |
|---|---|---|
| 68 | 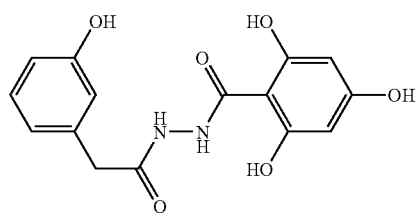 | 237-238 |
| 69 | 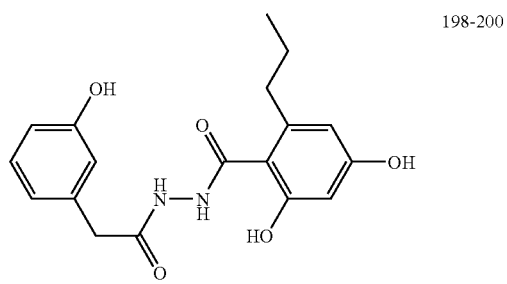 | 198-200 |
| 70 | 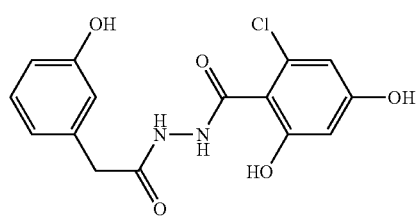 | 213-215 |
| 72 | 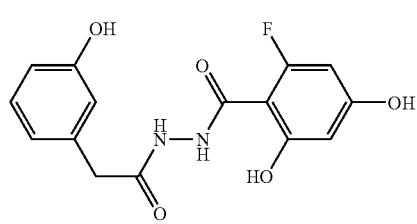 | 230-232 |
| 73 | 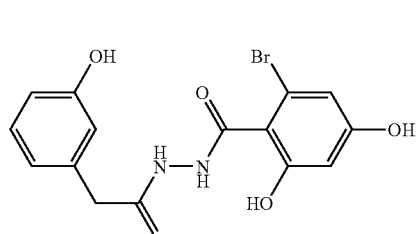 | 259 |
| 84 | 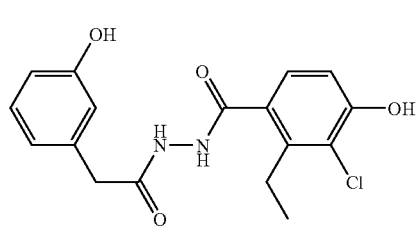 | 259 |

-continued

| No. | Structural formula | M.p. [° C.] |
|---|---|---|
| 87 | (structure: 3-hydroxyphenyl-CH2-C(=O)-NH-NH-C(=O)-[2-hydroxy-3-methyl-6-...benzene with OH]) | 240 |

The compounds according to the invention and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials can also be formed in situ by not isolating them from the reaction mixture, but instead immediately converting them further into the compounds according to the invention.

The starting compounds are generally known. If they are novel, however, they can be prepared by methods known per se.

Compounds of the formula I can preferably be obtained by reacting a hydrazide of the formula II with a compound of the formula III.

The reaction is carried out by methods which are known to the person skilled in the art. The reaction is generally carried out in an inert solvent, optionally in the presence of an acid-binding agent, preferably an organic base, such as DIPEA, triethylamine, dimethylaniline, pyridine or quinoline, or an excess of the carboxyl component of the formula Ill.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particularly preferred solvents are water or DMF.

The addition of an alkali or alkaline-earth metal hydroxide, carbonate or bicarbonate or another salt of a weak acid of the alkali or alkaline-earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

In the compounds of the formula III, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart;).

Activated esters are advantageously formed in situ, for example by addition of HOBt or N-hydroxysuccinimide.

Compounds of the formula I can furthermore preferably be obtained by reacting a hydrazide of the formula IV with a compound of the formula V.

The reaction is generally carried out in an inert solvent, in the presence of an acid-binding agent, preferably an organic base, such as DIPEA, triethylamine, dimethylaniline, pyridine or quinoline, or an excess of the carboxyl component of the formula V.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

The addition of an alkali or alkaline-earth metal hydroxide, carbonate or bicarbonate or another salt of a weak acid of the alkali or alkaline-earth metals, preferably of potassium, sodium, calcium or caesium, may also be favourable.

Depending on the conditions used, the reaction time is between a few minutes and 14 days, the reaction temperature is between about −30° and 140°, normally between −10° and 90°, in particular between about 0° and about 70°.

In the compounds of the formula V, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart;).

Activated esters are advantageously formed in situ, for example by addition of HOBt or N-hydroxysuccinimide.

Compounds of the formula I can furthermore be obtained by converting a radical $R^1$, $R^2$, $R^3$, $R^4$, $R^5$, $R^6$, $R^7$, $R^8$ and/or $R^9$ into another radical $R^1$, $R^2$, $R^3$, $R^4$, $R^5$, $R^6$, $R^7$, $R^8$ and/or $R^9$ by, for example, cleaving an ether by hydrolysis or hydrogenolysis.

The cleavage of an ether is carried out by methods as are known to the person skilled in the art.

A standard method for ether cleavage, for example of a methyl ether, is the use of boron tribromide.

Hydrogenolytically removable groups, for example the cleavage of a benzyl ether, can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar.

Esters can be saponified, for example, using acetic acid or using NaOH or KOH in water, water/THF or water/dioxane at temperatures between 0 and 100°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active ingredients.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the human or animal, the precise condition which requires treatment, and its severity, the nature of the formulation and the method of administration, and is ultimately determined by the treating doctor or vet. However, an effective amount of a compound according to the invention for the treatment is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or more usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable derivatives, solvates and stereoisomers thereof, including mixtures thereof in all ratios, and at least one further medicament active ingredient.

The invention also relates to a set (kit) consisting of separate packs of
(a) an effective amount of a compound according to the invention and/or pharmaceutically usable derivatives, solvates and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable derivatives, solvates and stereoisomers thereof, including mixtures thereof in all ratios, and an effective amount of a further medicament active ingredient in dissolved or lyophilised form.

Use

The present compounds are suitable as pharmaceutical active ingredients for mammals, in particular for humans, in the treatment of SGK-induced diseases.

The invention thus relates to the use of compounds according to claim 1, and pharmaceutically usable derivatives, solvates and stereoisomers thereof, including mixtures thereof in all ratios, for the preparation of a medicament for the treatment of diseases in which the inhibition, regulation and/or modulation of kinase signal transduction plays a role.

Preference is given here to SGK.

Preference is given to the use of compounds according to claim 1, and pharmaceutically usable derivatives, solvates and stereoisomers thereof, including mixtures thereof in all ratios, for the preparation of a medicament for the treatment of diseases which are influenced by inhibition of SGKs by the compounds according to claim 1.

The present invention encompasses the use of the compounds according to claim 1 according to the invention and/or physiologically acceptable salts and solvates thereof for the preparation of a medicament for the treatment or prevention of diabetes (for example diabetes mellitus, diabetic nephropathy, diabetic neuropathy, diabetic angiopathy and microangiopathy), obesity, metabolic syndrome (dyslipidaemia), systemic and pulmonary hypertonia, cardiovascular diseases (for example cardiac fibroses after myocardial infarction, cardiac hypertrophy and cardiac insufficiency, arteriosclerosis) and renal diseases (for example glomerulosclerosis, nephrosclerosis, nephritis, nephropathy, electrolyte excretion disorder), generally in fibroses and inflammatory processes of any type (for example liver cirrhosis, pulmonary fibrosis, fibrosing pancreatitis, rheumatism and arthroses, Crohn's disease, chronic bronchitis, radiation fibrosis, sclerormatitis, cystic fibrosis, scarring, Alzheimer's disease).

The compounds according to the invention can also inhibit the growth of cancer, tumour cells and tumour metastases and are therefore suitable for tumour therapy.

The compounds according to the invention are furthermore used for the treatment of coagulopathies, such as, for example, dysfibrinogenaemia, hypoproconvertinaemia, haemophilia B, Stuart-Prower defect, prothrombin complex deficiency, consumption coagulopathy, hyperfibrinolysis, immunocoagulopathy or complex coagulopathies, and also in neuronal excitability, for example epilepsy. The compounds according to the invention can also be employed therapeutically in the treatment of glaucoma or a cataract.

The compounds according to the invention are furthermore used in the treatment of bacterial infections and in antiinfection therapy. The compounds according to the invention can also be employed therapeutically for increasing learning ability and attention.

Preference is given to the use of compounds according to claim 1, and pharmaceutically usable derivatives, solvates and stereoisomers thereof, including mixtures thereof in all ratios, for the preparation of a medicament for the treatment or prevention of diabetes, obesity, metabolic syndrome (dyslipidaemia), systemic and pulmonary hypertonia, cardiovascular diseases and renal diseases, generally in fibroses and inflammatory processes of any type, cancer, tumour cells, tumour metastases, coagulopathies, neuronal excitability, glaucoma, cataract, bacterial infections and in anti-infection therapy, for increasing learning ability and attention, and for the treatment and prophylaxis of cell ageing and stress.

Diabetes is preferably diabetes mellitus, diabetic nephropathy, diabetic neuropathy, diabetic angiopathy and microangiopathy.

Cardiovascular diseases are preferably cardiac fibroses after myocardial infarction, cardiac hypertrophy, cardiac insufficiency and arteriosclerosis.

Renal diseases are preferably glomerulosclerosis, nephrosclerosis, nephritis, nephropathy and electrolyte excretion disorder.

Fibroses and inflammatory processes are preferably liver cirrhosis, pulmonary fibrosis, fibrosing pancreatitis, rheumatism and arthroses, Crohn's disease, chronic bronchitis, radiation fibrosis, sclerormatitis, cystic fibrosis, scarring, Alzheimer's disease.

Assays

The compounds according to the invention described in the examples were tested in the assays described below and were found to have kinase-inhibitory activity. Further assays are known from the literature and could easily be performed by the person skilled in the art (see, for example, Dhanabal et al., Cancer Res. 59:189-197; Xin et al., J. Biol. Chem. 274:9116-9121; Sheu et al., Anticancer Res. 18:4435-4441; Ausprunk et al., Dev. Biol. 38:237-248; Gimbrone et al., J. Natl. Cancer Inst. 52:413-427; Nicosia et al., In Vitro 18:538-549).

Above and below, all temperatures are indicated in ° C. In the following examples, "conventional work-up" means: if necessary, water is added, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS):
- EI (electron impact ionisation) M+
- FAB (fast atom bombardment) (M+H)+
- ESI (electrospray ionisation) (M+H)+ (unless indicated otherwise)

EXAMPLE 1

Preparation of N'-[2-(3-hydroxyphenyl)acetyl]-2-ethyl-4-hydroxybenzohydrazide ("60")

1.1

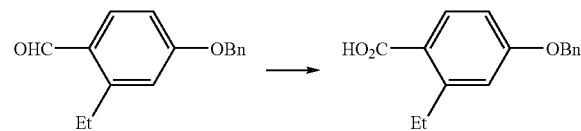

An aqueous solution (750 ml) of 85 g of NaClO₂ and 90 g of NaH₂PO₄ is added dropwise with cooling and stirring to 120 g of 4-benzyloxy-2-ethylbenzaldehyde, dissolved in 1 l of DMSO, during which the temperature should not rise above 35° C. The mixture is stirred at RT for a further 3 h, and the precipitate formed is filtered off with suction. The solid is then dissolved in 600 ml of EtOAc, dried and re-evaporated. The residue is crystallised from (Me₂CH)₂O, giving 4-benzyloxy-2-ethylbenzoic acid; yield 96.2 g (75%); m.p. 132-133°.

1.2

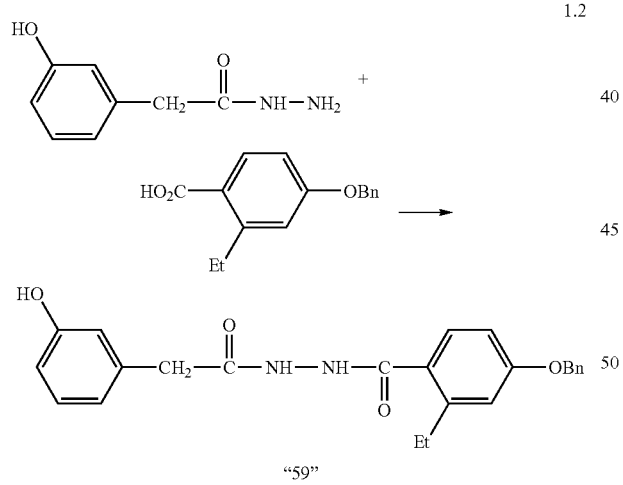

"59"

1.6 g of 4-benzyloxy-2-ethylbenzoic acid is refluxed with 4 ml of SOCl₂ until a clear solution forms. The SOCl₂ is stripped off, the mixture is subsequently evaporated to dryness a further 2× with CH₂Cl₂. The acid chloride is then dissolved in 3 ml of DMF, and 1.14 g of (3-hydroxyphenyl)acetohydrazide are added. The mixture is stirred at 40° C. for 2 hours and added to H₂O, and stirring is continued. The precipitated substance is filtered off with suction and dried, giving N'-[2-(3-hydroxyphenyl)acetyl]-4-benzyloxy-2-ethylbenzohydrazide ("59"); yield 1.49 g (59%); m.p. 190-191°.

1.3

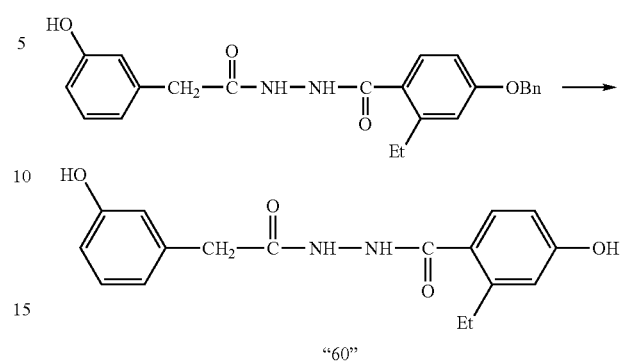

"60"

57.4 g of N'-[2-(3-hydroxyphenyl)acetyl]-4-benzyloxy-2-ethylbenzohydrazide are dissolved in 1.5 l of THF and hydrogenated for 24 h. The catalyst (5% Pd/C, 35 g) is added in 3 portions. The catalyst is filtered off with suction, the solution is evaporated, and the residue is crystallised from MeCN, giving 41.1 g of "60" (92%); m.p. 199-200°.

EXAMPLE 2

Preparation of N'-[2-(3-hydroxyphenyl)acetyl]-3,5-dihydroxy-4'-methylbiphenyl-2-carbohydrazide ("65")

2.1

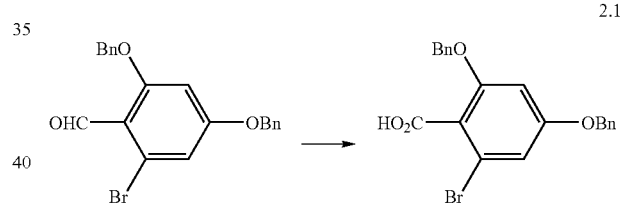

The reaction is carried out analogously to Example 1.1, giving 2,4-bis-benzyloxy-6-bromobenzoic acid, m.p. 152-154°.

2.2

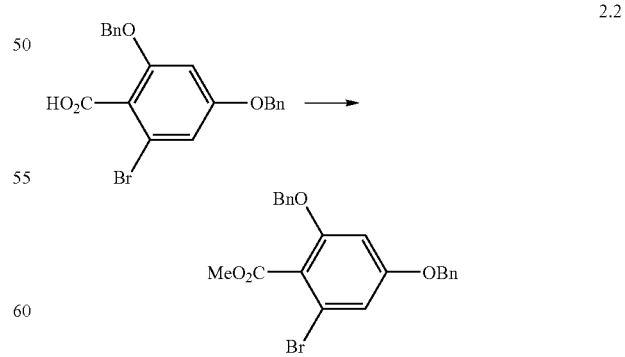

47 g of 2,4-bisbenzyloxy-6-bromobenzoic acid, 9 ml of MeI and 40 g of K₂CO₃ are stirred at 50° C. for 2 h in 150 ml of DMF. The mixture is then diluted with H₂O, extracted 3× with EtOAc, dried, evaporated, and the residue is crystallised using (Me$_2$CH)$_2$O. Yield: 37 g of methyl 2,4-bis-benzyloxy-6-bromobenzoate (76%); m.p. 90-91°.

2.3

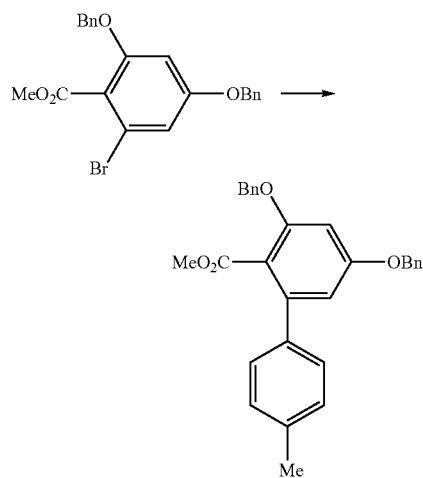

1.28 g of methyl 2,4-bisbenzyloxy-6-bromobenzoate, 540 mg of p-tolylboronic acid, 1.2 g of sodium tetraborate.10H$_2$O, 42.1 mg of bis-(triphenylphosphine)palladium(II) chloride and 0.01 ml of NH$_2$NH$_2$.H$_2$O are heated under reflux for 6 h with 10 ml of THF and 5 ml of H$_2$O. A further 200 mg of boronic acid and 400 mg of sodium tetraborate.10H$_2$O are added, and the mixture is heated for a further 4 h. The THF is stripped off, the residue is diluted with H$_2$O and extracted 3× with EtOAc. The combined organic extracts are dried, evaporated and chromatographed over silica gel. The clean fractions crystallise in the ice box over (Me$_2$CH)$_2$O. Yield: 300 mg of methyl 3,5-bisbenzyloxy-4'-methylbiphenyl-2-carboxylate (23%); m.p. 120°.

2.4

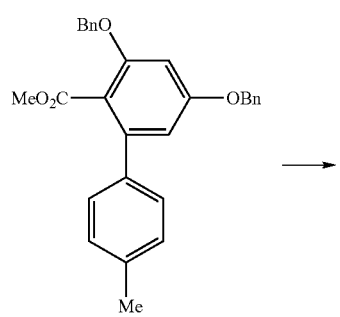

820 mg of methyl 3,5-bisbenzyloxy-4'-methylbiphenyl-2-carboxylate, 1.5 ml of 32% NaOH and 7 ml of Me$_2$CHOH are stirred at 135° C. for 2 h in a sealed glass Carius tube. The solution is evaporated, diluted with H$_2$O, acidified using HCl and extracted 3× with EtOAc. The combined organic extracts are dried, evaporated and triturated with (Me$_2$CH)$_2$O. Yield: 450 mg of 3,5-bisbenzyloxy-4'-methylbiphenyl-2-carboxylic acid (57%); m.p. 307-310°.

2.5

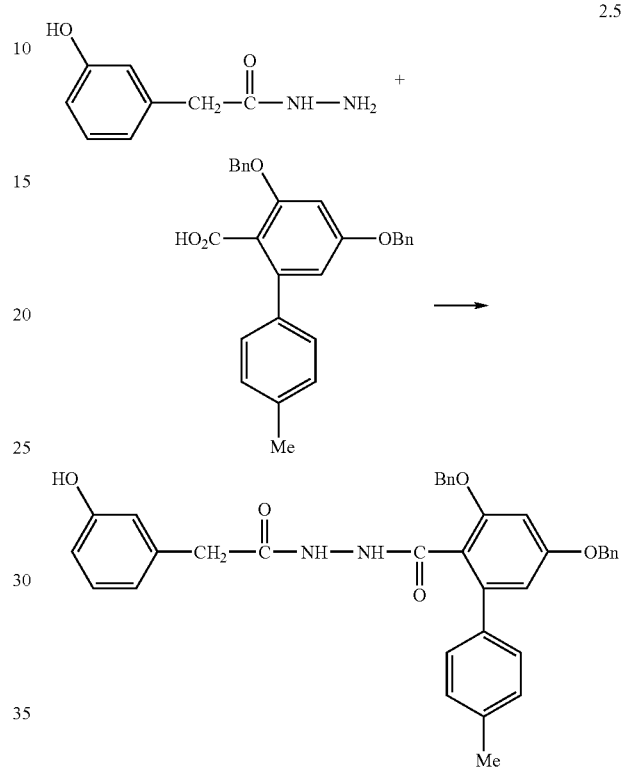

295 mg of 3,5-bisbenzyloxy-4'-methylbiphenyl-2-carboxylic acid, 190 mg of 1-ethyl-3-(3-dimethylaminopropyl)carbodiimide (WSCD) and 110 mg of 1-hydroxybenzotriazole (HOBt) are stirred at 36° C. for 4 h in 1.5 ml of DMF. 200 mg of (3-hydroxyphenyl)acetohydrazide are added, and stirring is continued overnight at 36° C. The reaction mixture is diluted with 2 ml of MeOH, stirred into H$_2$O, and the precipitate is filtered off with suction. The solid is dissolved in 20 ml of EtOAc, dried and crystallised from Me$_2$CHOH/Et$_2$O. Yield: 240 mg of N'-[2-(3-hydroxyphenyl)acetyl]-3,5-bisbenzyloxy-4'-methylbiphenyl-2-carbohydrazide (60%); m.p. 168-169°.

2.6

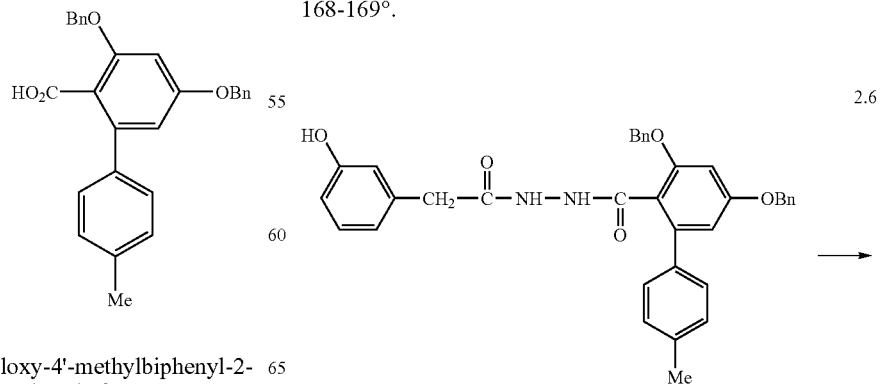

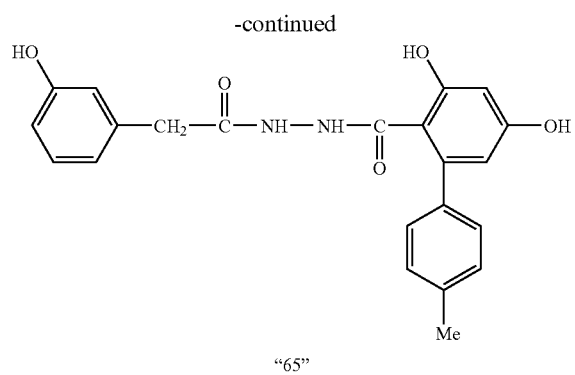

"65"

N'-[2-(3-Hydroxyphenyl)acetyl]-3,5-bisbenzyloxy-4'-methylbiphenyl-2-carbohydrazide is hydrogenated analogously to Example 1.3, giving "65" (22%); m.p. 97° (decomposition).

EXAMPLE 3

Preparation of N'-[2-(3-hydroxyphenyl)acetyl]-2,4,6-trihydroxybenzohydrazide ("68")

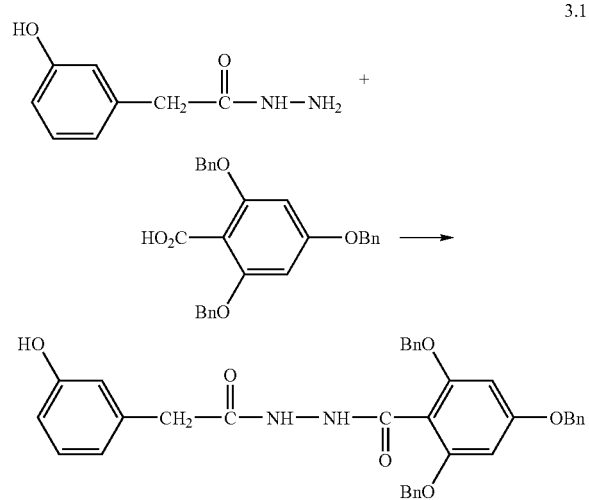

The coupling of 2,4,6-tribenzyloxybenzoic acid to (3-hydroxyphenyl)acetohydrazide is carried out analogously to Example 2.5, giving N'-[2-(3-hydroxyphenyl)acetyl]-2,4,6-tribenzyloxybenzohydrazide, yield 40%; m.p. 154-155°.

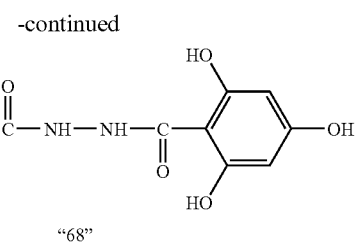

"68"

N'-[2-(3-hydroxyphenyl)acetyl]-2,4,6-tribenzyloxybenzohydrazide is hydrogenated analogously to Example 1.3, giving "68" (yield 81%); m.p. 237-238°.

EXAMPLE 4

Preparation of N'-[2-(3,5-dihydroxyphenyl)acetyl]-2,4-dihydroxy-6-methylbenzohydrazide ("67")

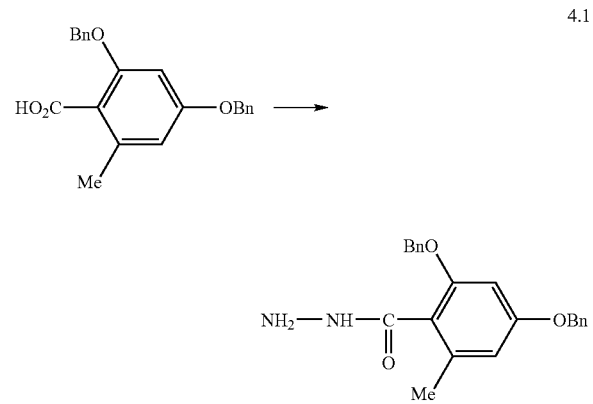

$N_2H_5OH$ is monoacylated analogously to Example 2.5 using 2,4-dibenzyloxy-6-methylbenzoic acid. Yield: 2,4-dibenzyloxy-6-methylbenzohydrazide (63%); m.p. 136-137°.

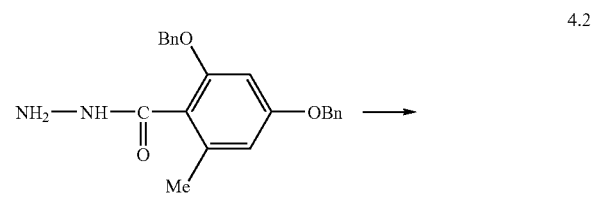

2,4-Dibenzyloxy-6-methylbenzohydrazide is hydrogenated analogously to Example 1.3. Yield: 2,4-dihydroxy-6-methylbenzohydrazide (89%); m.p. 226° (decomposition).

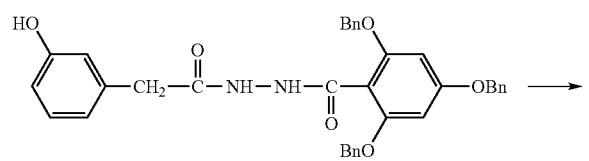

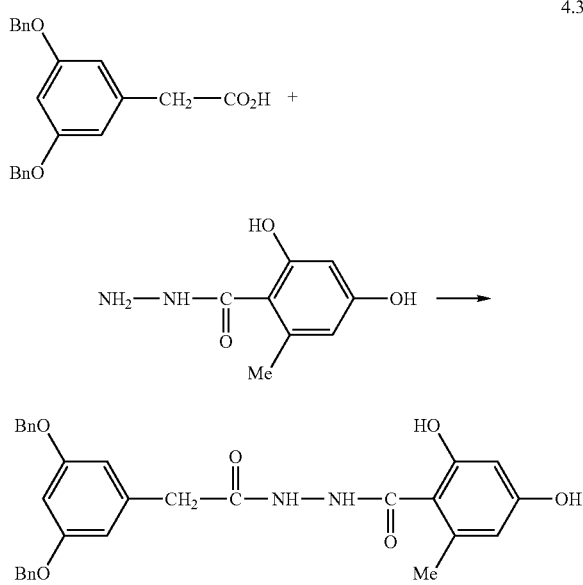

The coupling of (3,5-bisbenzyloxyphenyl)acetic acid to 2,4-dihydroxy-6-methylbenzohydrazide is carried out analogously to Example 2.5. Yield: N'-[2-(3,5-dibenzyloxyphenyl)acetyl]-2,4-dihydroxy-6-methylbenzohydrazide (39%).

4.4

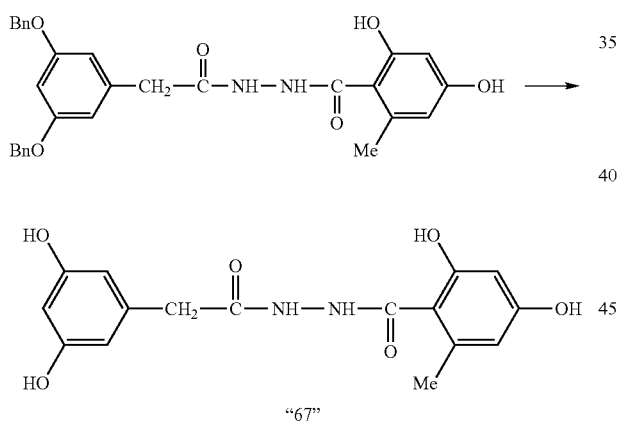

"67"

4.3

N'-[2-(3,5-dibenzyloxyphenyl)acetyl]-2,4-dihydroxy-6-methylbenzohydrazide is hydrogenated analogously to Example 1.3. Yield: "67" (83%); m.p. 281° (decomposition).

EXAMPLE 5

5.1 An analogous procedure to Example 2.5 gives N'-[2-(3-hydroxyphenyl)acetyl]-2-chloro-4,6-dimethoxybenzohydrazide ("69a").

5.2 9 g of "69a" are suspended in 30 ml of dichloromethane. 40 ml of $BBr_3$ are added dropwise with ice-cooling. After 48 hours at room temperature, 200 ml of ice-water are stirred in. The mixture is subjected to conventional work-up, separated over silica gel by means of a CombiFlash COMPANION instrument and crystallised from diethyl ether, giving 3.3 g of N'-[2-(3-hydroxyphenyl)acetyl]-2-chloro-4,6-dihydroxybenzohydrazide ("70"), m.p. 217°

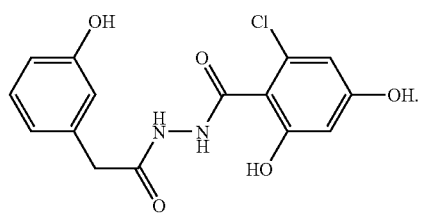

"70"

EXAMPLE 6

6.1 An analogous procedure to Example 2.5 and 2.6 gives N'-[2-(3-hydroxyphenyl)acetyl]-4-hydroxy-3-nitrobenzohydrazide ("74"), m.p. 190-193°.

6.2 "74" is hydrogenated by standard methods using Pd/C in THF. The catalyst and the solvent are separated off. A little methanol/HCl is added to the residue. The precipitate is separated off and dried, giving N'-[2-(3-hydroxyphenyl)acetyl]-3-amino-4-hydroxybenzohydrazide ("78"), yield 79%, m.p. 264-265°.

The following compounds are obtained analogously

| No. | Structural formula | m.p. [° C.] |
|---|---|---|
| 1 | | 233-235 |

-continued

| No. | Structural formula | m.p. [° C.] |
|---|---|---|
| 2 | 3-HOC6H4CH2C(O)NHNHC(O)-C6H4-4-OCH2C6H5 | 199-200 |
| 3 | 3-HOC6H4CH2C(O)NHNHC(O)-C6H4-4-OH | 207-208 |
| 4 | 3-HOC6H4CH2C(O)NHNHC(O)-C6H4-3-OCH2C6H5 | 152-153 |
| 5 | 3-HOC6H4CH2C(O)NHNHC(O)-C6H4-2-OH | 214-215 |
| 6 | 3-HOC6H4CH2C(O)NHNHC(O)-C6H4-3-OH | 224-225 |
| 7 | 3-HOC6H4CH2C(O)NHNHC(O)-C6H3-2-Cl-4-OCH2C6H5 | 162-164 |

-continued

| No. | Structural formula | m.p. [° C.] |
|---|---|---|
| 8 | | 165-166 |
| 9 | | 174-175 |
| 10 | | 199-200 |
| 11 | | 226-227 |
| 12 | | 198-199 |
| 13 | | 171-172 |

-continued

| No. | Structural formula | m.p. [° C.] |
|---|---|---|
| 14 | | 193-194 |
| 15 | | 212-213 |
| 16 | | 189-190 |
| 17 | | 181-182 |
| 18 | | 156-157 |
| 19 | | 201-202 |
| 20 | | 179 |

-continued

| No. | Structural formula | m.p. [° C.] |
| --- | --- | --- |
| 21 | | 154-155 |
| 22 | | 175-176 |
| 23 | | 172 |
| 24 | | 183-184 |
| 25 | | 202-203 |
| 26 | | 248-249 |
| 27 | | 190-191 |

-continued

| No. | Structural formula | m.p. [° C.] |
|---|---|---|
| 28 | | 229 |
| 29 | | 197-198 |
| 30 | | 197-198 |
| 31 | | 182-183 |
| 32 | | 201-202 |
| 33 | | 194-195 |
| 34 | | 210-211 |

-continued

| No. | Structural formula | m.p. [° C.] |
|---|---|---|
| 35 | 3-hydroxyphenylacetic acid N'-(4-hydroxy-2-methoxybenzoyl)hydrazide | 208-209 |
| 36 | 3-hydroxyphenylacetic acid N'-(4-methoxybenzoyl)hydrazide | 158-159 |
| 37 | 3-hydroxyphenylacetic acid N'-(3-fluorobenzoyl)hydrazide | 176-177 |
| 38 | 3-hydroxyphenylacetic acid N'-(2,6-difluorobenzoyl)hydrazide | 191-192 |
| 39 | 3-hydroxyphenylacetic acid N'-(3-cyanobenzoyl)hydrazide | 181.5-182.5 |
| 40 | 3-hydroxyphenylacetic acid N'-(2,3-dichlorobenzoyl)hydrazide | 220-221 |
| 41 | 3-hydroxyphenylacetic acid N'-(3,4-difluorobenzoyl)hydrazide | 164 |

-continued

| No. | Structural formula | m.p. [° C.] |
|---|---|---|
| 42 | | 130-132 |
| 43 | | 183-184 |
| 44 | | 155-156 |
| 45 | | 148-150 |
| 46 | | 165-166 |
| 47 | | 195-196 |

-continued

| No. | Structural formula | m.p. [° C.] |
|---|---|---|
| 48 | 3-hydroxyphenylacetic acid N'-(3-trifluoromethoxybenzoyl)hydrazide | 256-257 |
| 49 | 3-hydroxyphenylacetic acid N'-(2-nitrobenzoyl)hydrazide | 206-207 |
| 50 | 3-hydroxyphenylacetic acid N'-(4-chlorobenzoyl)hydrazide | 223 |
| 51 | 3-hydroxyphenylacetic acid N'-benzoylhydrazide | 162-163 |
| 52 | 3-hydroxyphenylacetic acid N'-(3-(dichloromethyl)benzoyl)hydrazide | 154-155 |
| 53 | 3-hydroxyphenylacetic acid N'-(3-trifluoromethylbenzoyl)hydrazide | 161-162 |
| 54 | 3-hydroxyphenylacetic acid N'-(4-(chloromethyl)benzoyl)hydrazide | 175-176 |

-continued

| No. | Structural formula | m.p. [° C.] |
|---|---|---|
| 55 | | 138-139 |
| 56 | | 222-223 |
| 57 | | 226-227 |
| 58 | | 165-166 |
| 61 | | 193-194 |
| 62 | | 251 |

-continued
| No. | Structural formula | m.p. [° C.] |
|---|---|---|
| 63 | 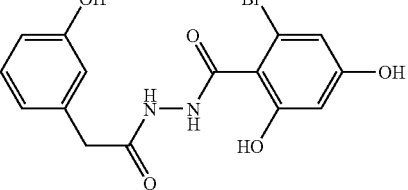 | 226-227 |
| 64 | 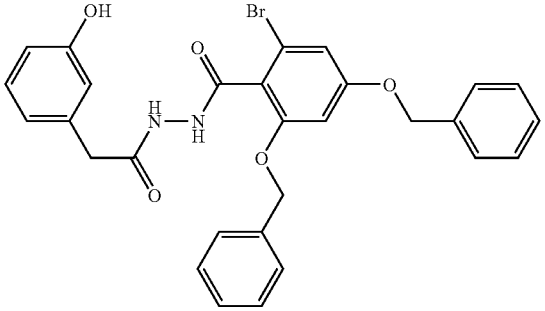 | 194-195 |
| 66 | 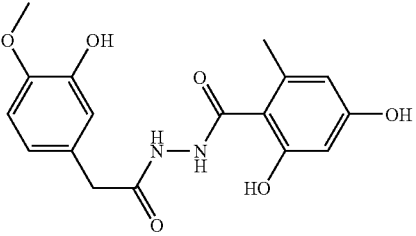 | 232-233 |
| 69 | 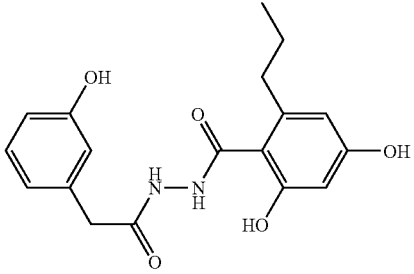 | 198-200 |
| 71 | 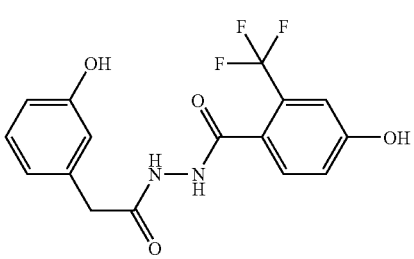 | 210-212 |
| 72 | 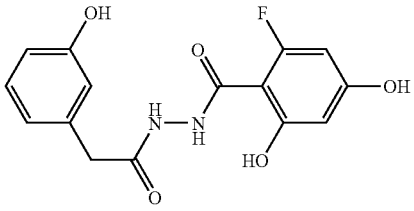 | 230-232 |

-continued
| No. | Structural formula | m.p. [° C.] |
|---|---|---|
| 73 | 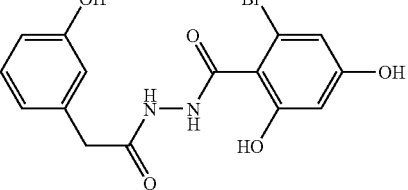 | 259 |
| 75 | 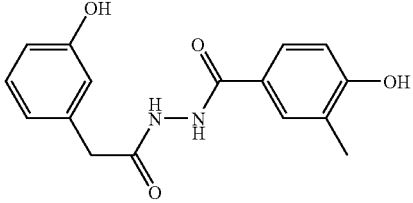 | 207-208 |
| 76 | 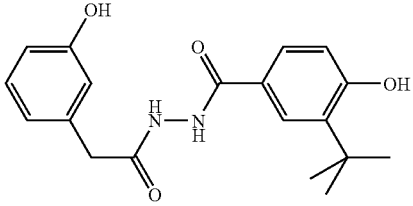 | 154-157 |
| 77 | 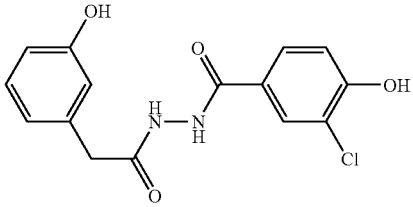 | 230-231 |
| 79 | 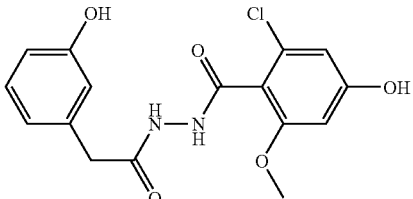 | 105-106 |
| 80 | 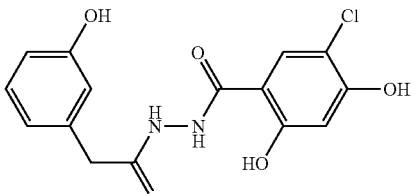 | 269-270 |
| 81 | 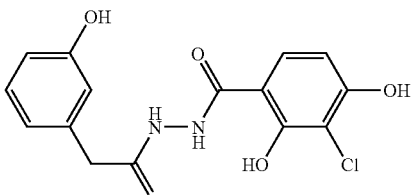 | 252-253 |

-continued
| No. | Structural formula | m.p. [° C.] |
|---|---|---|
| 82 | 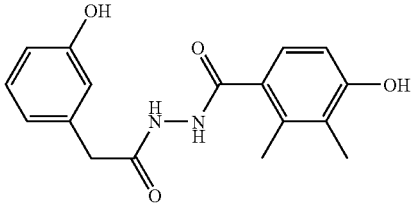 | 251 |
| 83 | 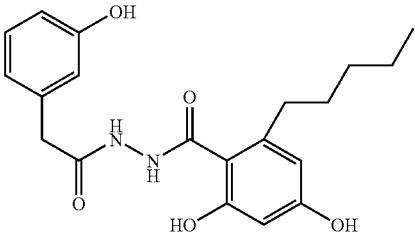 | 230 |
| 84 | 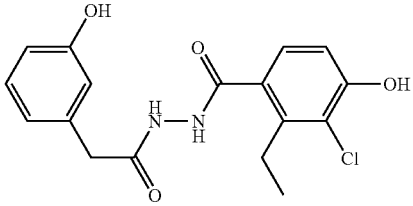 | 259 |
| 85 | 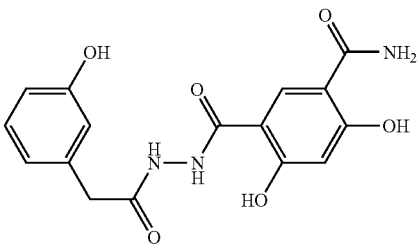 | 260-261 |
| 86 | 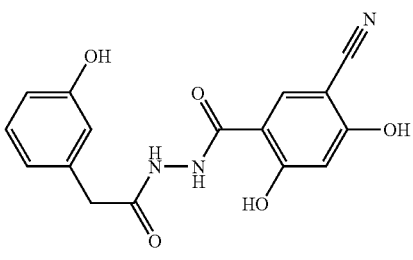 | 258 |
| 87 | 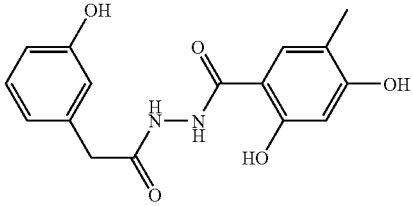 | 240 |

-continued

| No. | Structural formula | m.p. [° C.] |
|---|---|---|
| 88 | (structure: 3-hydroxyphenyl-CH₂-C(O)-NH-NH-C(O)-benzene with Cl, OH, CF₃ substituents) | 200-202 |

The following examples relate to pharmaceutical compositions:

EXAMPLE A

Injection Vials

A solution of 100 g of an active ingredient according to the invention and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient according to the invention, 9.38 g of NaH₂PO₄.2H₂O, 28.48 g of Na₂HPO₄.12H₂O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient according to the invention are mixed with 99.5 g of Vaseline under aseptic conditions.

EXAMPLE E

Tablets

A mixture of 1 kg of active ingredient, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient are introduced into hard gelatine capsules in a conventional manner in such a way that each capsule contains 20 mg of the active ingredient.

EXAMPLE H

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:

1. Compounds of the formula I (structure I: HO-phenyl(R⁶,R⁷,R⁸,R⁹)-CH₂-C(O)-NH-NH-C(O)-phenyl(R¹,R²,R³,R⁴,R⁵))

in which $R^1$, $R^2$, $R^3$, $R^4$, $R^5$, $R^6$, $R^7$, $R^8$, and $R^9$ each, independently of one another, denote H, A, OSO₂A, Hal, NO₂, OR¹⁰, N(R¹⁰)₂, CN, —[C(R¹⁰)₂]ₙCOOR¹⁰, O—[C(R¹⁰)₂]₀COOR¹⁰, SO₃H, —[C(R¹⁰)₂]ₙAr, —CO—Ar, O—[C(R¹⁰)₂]ₙAr, —[C(R¹⁰)₂]ₙHet, —[C(R¹⁰)₂]ₙC≡CH, O—[C(R¹⁰)₂]ₙC≡CH, —[C(R¹⁰)₂]ₙCON(R¹⁰)₂, —[C(R¹⁰)₂]ₙCONR¹⁰N(R¹⁰)₂, O—[C(R¹⁰)₂]ₙCON(R¹⁰)₂, O—[C $(R^{10})_2]_o CONR^{10}N(R^{10})_2$, $NR^{10}COA$, $NR^{10}CON(R^{10})_2$, $NR^{10}SO_2A$, $N(SO_2A)_2$, $COR^{10}$, $S(O)_m Ar$, $SO_2NR^{10}$ or $S(O)_m A$, or $R^1$ and $R^2$, $R^2$ and $R^3$, $R^3$ and $R^4$ or $R^4$ and $R^5$ together also denote CH=CH—CH=CH, A denotes unbranched or branched alkyl having 1-6 C atoms, in which 1-7H atoms may be replaced by F, or cyclic alkyl having 3-7 C atoms, Ar denotes phenyl, naphthyl or biphenyl, each of which is unsubstituted or mono-, di- or trisubstituted by Hal, A, $OR^{10}$, $N(R^{10})_2$, $NO_2$, CN, phenyl, $CON(R^{10})_2$, $NR^{10}COA$, $NR^{10}CON(R^{10})_2$, $NR^{10}SO_2A$, $COR^{10}$, $SO_2N(R^{10})_2$, $S(O)_m A$, $—[C(R^{10})_2]_n—COOR^{10}$ and/or $—O[C(R^{10})_2]_o—COOR^{10}$, Het denotes a mono- or bicyclic saturated, unsaturated or aromatic heterocycle having 1 to 4 N, O and/or S atoms, which may be mono-, di- or trisubstituted by Hal, A, $OR^{10}$, $N(R^{10})_2$, $NO_2$, CN, $COOR^{10}$, $CON(R^{10})_2$, $NR^{10}COA$, $NR^{10}SO_2A$, $COR^{10}$, $SO_2NR^{10}$, $S(O)_m A$, =S, $=NR^{10}$ and/or =O (carbonyl oxygen), $R^{10}$ denotes H or A, Hal denotes F, Cl, Br or I, m denotes 0, 1 or 2, n denotes 0, 1, 2 or 3, and o denotes 1, 2 or 3, or pharmaceutically usable salts or stereoisomers thereof, including mixtures thereof in all ratios.

2. Compounds according to claim 1 in which
$R^1$ denotes H, A, Hal, $NO_2$, $OR^{10}$, $—[C(R^{10})_2]_n Ar$ or $O—[C(R^{10})_2]_n Ar$, or pharmaceutically usable salts or stereoisomers thereof, including mixtures thereof in all ratios.

3. Compounds according to claim 1 in which
$R^2$ denotes H, A, Hal, CN, $NO_2$, $OR^{10}$, $—[C(R^{10})_2]_n Ar$ or pharmaceutically usable salts or stereoisomers thereof, including mixtures thereof in all ratios.

4. Compounds according to claim 1 in which
$R^3$ denotes H, A, Hal, $NO_2$, $OR^{10}$, $—[C(R^{10})_2]_n Ar$, $O—[C(R^{10})_2]_n Ar$, $—[C(R^{10})_2]_n COOR^{10}$ or $S(O)_m A$, or pharmaceutically usable salts or stereoisomers thereof, including mixtures thereof in all ratios.

5. Compounds according to claim 1 in which
$R^4$ denotes H, A, Hal, $CONH_2$, CN, $NO_2$ or $OR^{10}$, or pharmaceutically usable salts or stereoisomers thereof, including mixtures thereof in all ratios.

6. Compounds according to claim 1 in which
$R^5$ denotes H, A, Hal, $OR^{10}$, $—[C(R^{10})_2]_n Ar$ or $O—[C(R^{10})_2]_n Ar$, or pharmaceutically usable salts or stereoisomers thereof, including mixtures thereof in all ratios.

7. Compounds according to claim 1 in which
$R^6$ denotes H or A, or pharmaceutically usable salts or stereoisomers thereof, including mixtures thereof in all ratios.

8. Compounds according to claim 1 in which
$R^7$ denotes H, A or $OR^{10}$, or pharmaceutically usable salts or stereoisomers thereof, including mixtures thereof in all ratios.

9. Compounds according to claim 1 in which
$R^8$ denotes H, A or $OR^{10}$, or pharmaceutically usable salts or stereoisomers thereof, including mixtures thereof in all ratios.

10. Compounds according to claim 1 in which
$R^9$ denotes H or A, or pharmaceutically usable salts or stereoisomers thereof, including mixtures thereof in all ratios.

11. Compounds according to claim 1 in which
Ar denotes phenyl which is unsubstituted or mono-, di- or trisubstituted by Hal and/or A, or pharmaceutically usable salts or stereoisomers thereof, including mixtures thereof in all ratios.

12. Compounds according to claim 1 in which
Het denotes a monocyclic saturated, unsaturated or aromatic heterocycle having 1 to 2 N and/or O atoms, which may be unsubstituted or mono-, di- or trisubstituted by A, Hal, OH and/or OA, or pharmaceutically usable salts or stereoisomers thereof, including mixtures thereof in all ratios.

13. Compounds according to claim 1 in which
Het denotes a monocyclic saturated heterocycle having 1 to 2 N and/or O atoms, which may be unsubstituted or mono- or disubstituted by A, or pharmaceutically usable salts or stereoisomers thereof, including mixtures thereof in all ratios.

14. Compounds according to claim 1 in which
Het denotes furyl, thienyl, pyrrolyl, imidazolyl, pyridyl, pyrimidinyl, pyrazolyl, thiazolyl, indolyl, pyrrolidinyl, piperidinyl, morpholinyl or piperazinyl, each of which is unsubstituted or mono-, di- or trisubstituted by A, Hal, OH and/or OA, or pharmaceutically usable salts or stereoisomers thereof, including mixtures thereof in all ratios.

15. Compounds according to claim 1 in which
$R^1$ denotes H, A, Hal, $NO_2$, $OR^{10}$, $—[C(R^{10})_2]_n Ar$ or $O—[C(R^{10})_2]_n Ar$, $R^2$ denotes H, A, Hal, CN, $N(R^{10})_2$, $NO_2$, $OR^{10}$, $—[C(R^{10})_2]_n Ar$ or $O—[C(R^{10})_2]_n Ar$, $R^3$ denotes H, A, Hal, $NO_2$, $OR^{10}$, $—[C(R^{10})_2]_n Ar$, $O—[C(R^{10})_2]_n Ar$, $—[C(R^{10})_2]_n COOR^{10}$ or $S(O)_m A$, $R^4$ denotes H, A, Hal, $CONH_2$, CN, $NO_2$ or $OR^{10}$, $R^5$ denotes H, A, Hal, $OR^{10}$, $—[C(R^{10})_2]_n Ar$ or $O—[C(R^{10})_2]_n Ar$, $R^6$ denotes H, $R^7$ denotes H or $OR^{10}$, $R^8$ denotes H or $OR^{10}$, $R^9$ denotes H, or $R^1$ and $R^2$, $R^2$ and $R^3$, $R^3$ and $R^4$ or $R^4$ and $R^5$ together also denote CH=CH—CH=CH, A denotes unbranched or branched alkyl having 1-6 C atoms, in which 1-7H atoms may be replaced by F, Ar denotes phenyl which is unsubstituted or mono-, di- or trisubstituted by Hal and/or A, $R^{10}$ denotes H or A, Hal denotes F, Cl, Br or I, m denotes 0, 1 or 2, and n denotes 0, 1, 2 or 3, or pharmaceutically usable salts or stereoisomers thereof, including mixtures thereof in all ratios.

16. Compounds according to claim 1 in which
$R^1$ denotes OH, A or Hal, $R^2$ denotes H, A or Hal, $R^3$ denotes OH, $R^4$ denotes H, A or Hal, $R^5$ denotes H or OH, $R^6$ denotes H, $R^7$ denotes H, $R^8$ denotes H, $R^9$ denotes H, or $R^1$ and $R^2$, $R^2$ and $R^3$, $R^3$ and $R^4$ or $R^4$ and $R^5$ together also denote CH=CH—CH=CH, A denotes unbranched or branched alkyl having 1-6 C atoms, in which 1-7H atoms may be replaced by F, and Hal denotes F, Cl, Br or I, or pharmaceutically usable salts or stereoisomers thereof, including mixtures thereof in all ratios.

17. Compounds according to claim 1 selected from the following compounds:

| No. | Structural formula |
|---|---|
| 1 | |
| 2 | |
| 3 | |
| 4 | |
| 5 | |
| 6 | |
| 7 | |
| 8 | |
| 9 | |
| 10 | |
| 11 | |
| 12 | |

-continued

| No. | Structural formula |
|---|---|
| 13 | 3-hydroxyphenylacetic acid N'-(4-methoxy-2-methylbenzoyl)hydrazide |
| 14 | 3-hydroxyphenylacetic acid N'-(4-benzyloxy-2-methoxybenzoyl)hydrazide |
| 15 | 3-hydroxyphenylacetic acid N'-(2-bromo-5-chlorobenzoyl)hydrazide |
| 16 | 3-hydroxyphenylacetic acid N'-(4-trifluoromethoxybenzoyl)hydrazide |
| 17 | 3-hydroxyphenylacetic acid N'-(2-methoxybenzoyl)hydrazide |
| 18 | 3-hydroxyphenylacetic acid N'-(3-methylbenzoyl)hydrazide |
| 19 | 3-hydroxyphenylacetic acid N'-(4-methoxycarbonylbenzoyl)hydrazide |

-continued

| No. | Structural formula |
|---|---|
| 20 | 3-hydroxyphenylacetic acid N'-(3-nitrobenzoyl)hydrazide |
| 21 | 3-hydroxyphenylacetic acid N'-(2-fluorobenzoyl)hydrazide |
| 22 | 3-hydroxyphenylacetic acid N'-(4-methylbenzoyl)hydrazide |
| 23 | 3-hydroxyphenylacetic acid N'-(2-chlorobenzoyl)hydrazide |
| 24 | 3-hydroxyphenylacetic acid N'-(3-chlorobenzoyl)hydrazide |
| 25 | 3-hydroxyphenylacetic acid N'-(2,4-dichlorobenzoyl)hydrazide |
| 26 | 3-hydroxyphenylacetic acid N'-(3,5-dinitrobenzoyl)hydrazide |

-continued

| No. | Structural formula |
|---|---|
| 27 | 3-hydroxyphenylacetic acid N'-(2-iodobenzoyl)hydrazide |
| 28 | 3-hydroxyphenylacetic acid N'-(4-bromobenzoyl)hydrazide |
| 29 | 3-hydroxyphenylacetic acid N'-(2,4-dimethoxybenzoyl)hydrazide |
| 30 | 3-hydroxyphenylacetic acid N'-(2-methylbenzoyl)hydrazide |
| 31 | 3-hydroxyphenylacetic acid N'-(4-fluorobenzoyl)hydrazide |
| 32 | 3-hydroxyphenylacetic acid N'-(2-naphthoyl)hydrazide |
| 33 | 3-hydroxyphenylacetic acid N'-(3-bromobenzoyl)hydrazide |

-continued

| No. | Structural formula |
|---|---|
| 34 | 3-hydroxyphenylacetic acid N'-(1-naphthoyl)hydrazide |
| 35 | 3-hydroxyphenylacetic acid N'-(4-hydroxy-2-methoxybenzoyl)hydrazide |
| 36 | 3-hydroxyphenylacetic acid N'-(4-methoxybenzoyl)hydrazide |
| 37 | 3-hydroxyphenylacetic acid N'-(3-fluorobenzoyl)hydrazide |
| 38 | 3-hydroxyphenylacetic acid N'-(2,6-difluorobenzoyl)hydrazide |
| 39 | 3-hydroxyphenylacetic acid N'-(3-cyanobenzoyl)hydrazide |
| 40 | 3-hydroxyphenylacetic acid N'-(2,3-dichlorobenzoyl)hydrazide |

-continued

| No. | Structural formula |
|---|---|
| 41 | |
| 42 | |
| 43 | |
| 44 | |
| 45 | |
| 46 | |
| 47 | |
| 48 | |
| 49 | |
| 50 | |
| 51 | |
| 53 | |
| 55 | |

| No. | Structural formula |
|---|---|
| 56 | 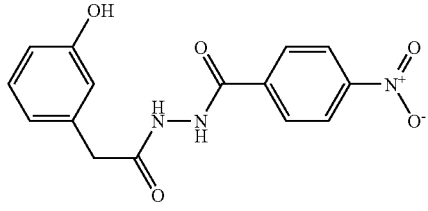 |
| 57 | 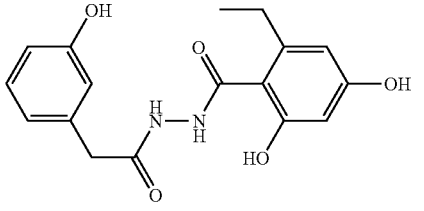 |
| 58 | 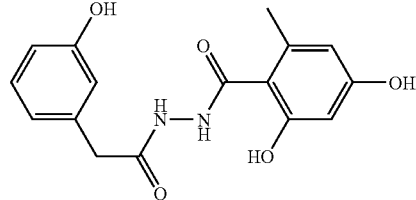 |
| 59 | 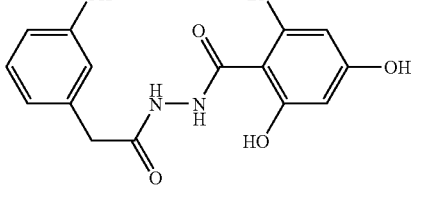 |
| 60 | 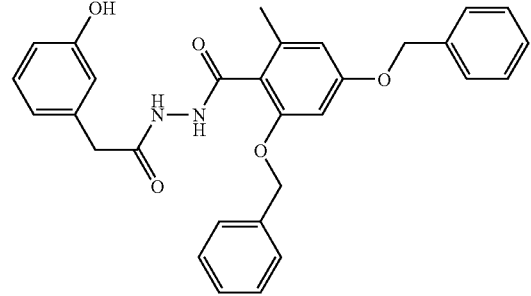 |
| 61 | 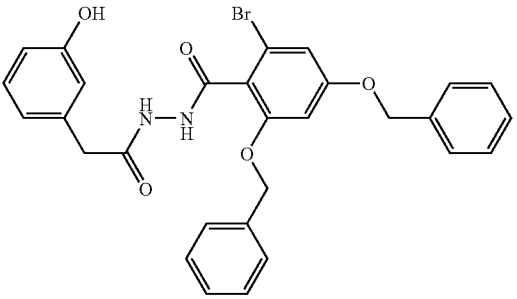 |
| No. | Structural formula |
|---|---|
| 62 | 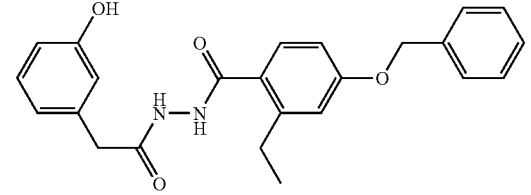 |
| 63 | 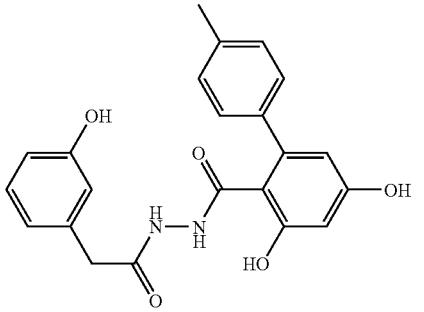 |
| 64 | 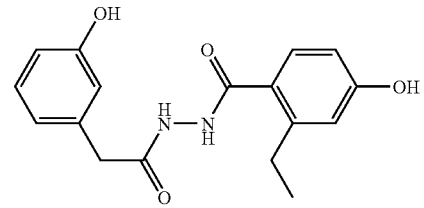 |
| 65 | 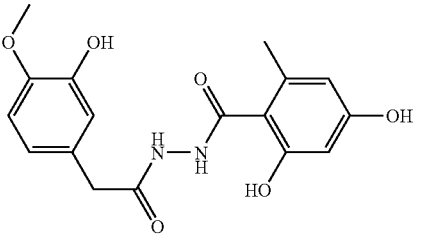 |
| 66 | 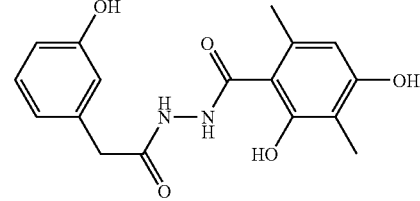 |
| 67 | 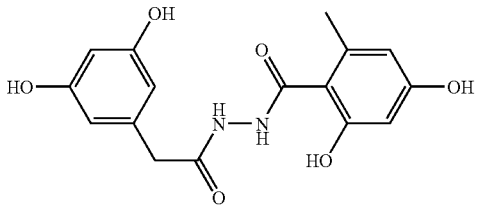 |

| No. | Structural formula |
|---|---|
| 68 | 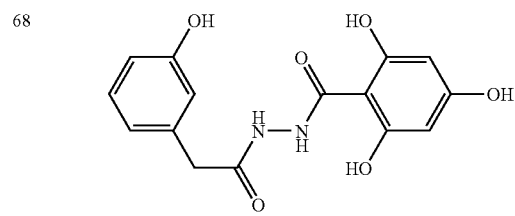 |
| 69 | 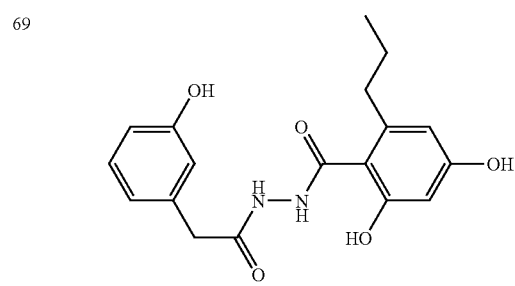 |
| 70 | 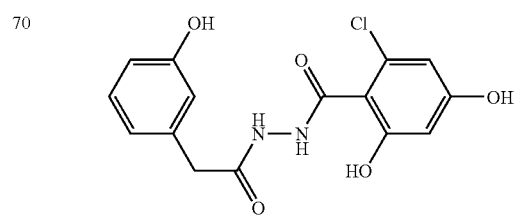 |
| 71 | 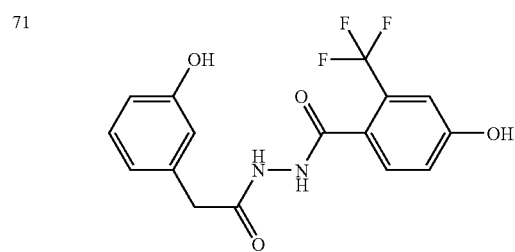 |
| 72 | 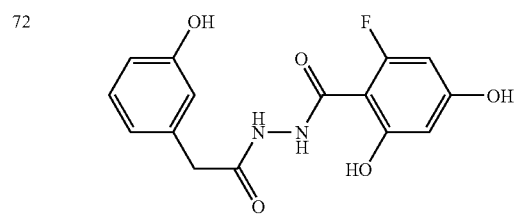 |
| 73 | 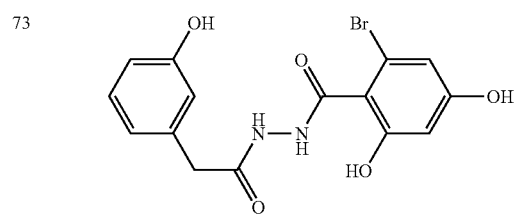 |
| No. | Structural formula |
|---|---|
| 74 | 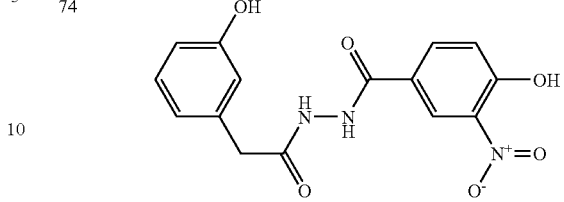 |
| 75 | 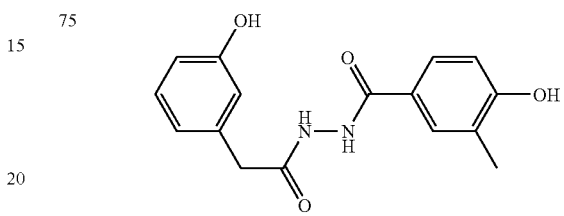 |
| 76 | 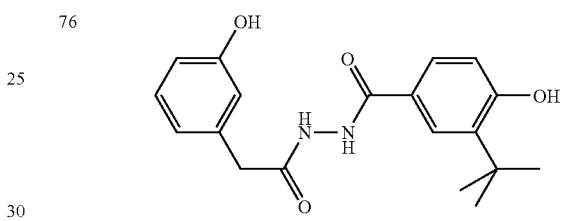 |
| 77 | 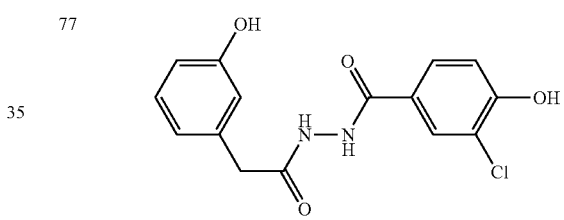 |
| 78 | 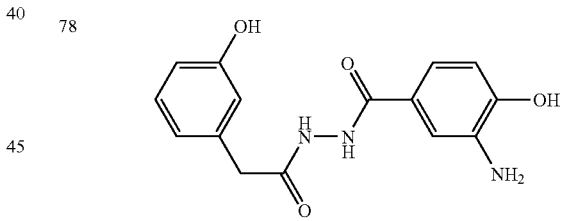 |
| 79 | 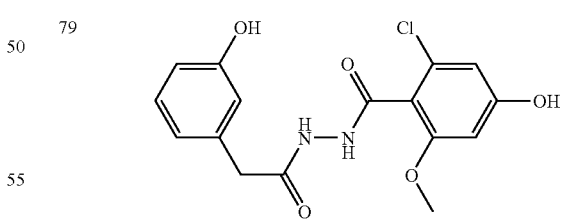 |
| 80 | 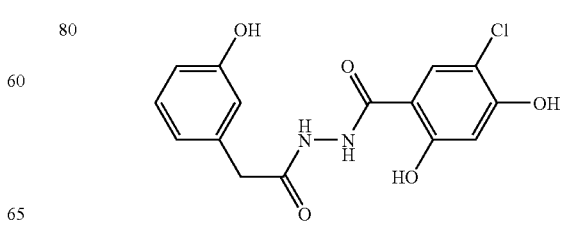 |

-continued

| No. | Structural formula |
|---|---|
| 81 | 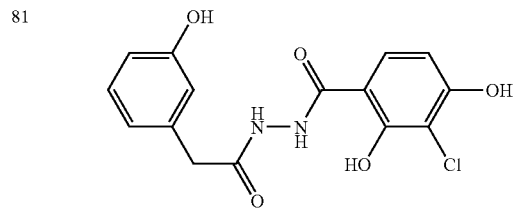 |
| 82 | 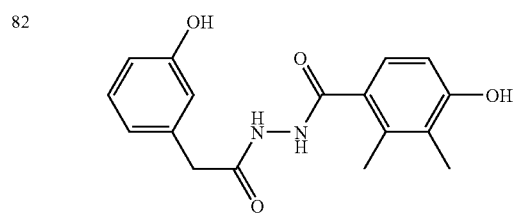 |
| 83 | 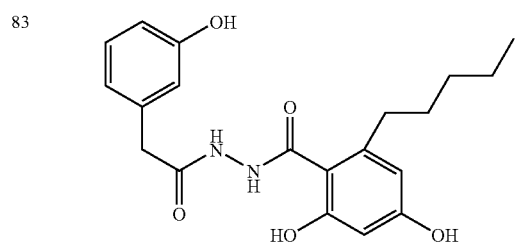 |
| 84 | 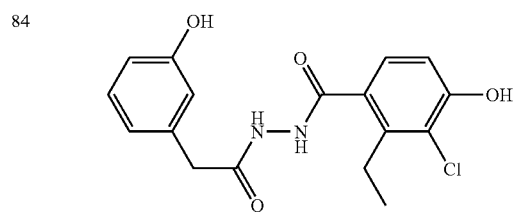 |
| 85 | 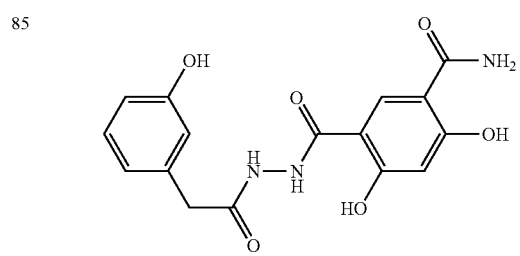 |
| 86 | 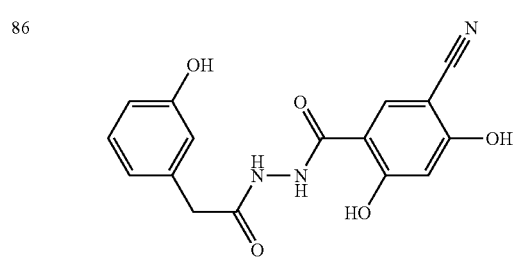 |

-continued

| No. | Structural formula |
|---|---|
| 87 | 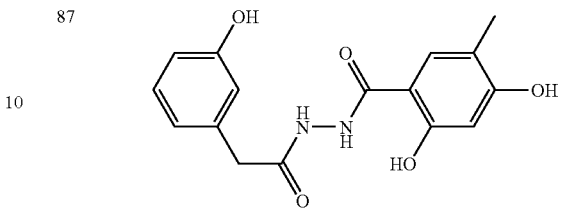 |
| | and |
| 88 | 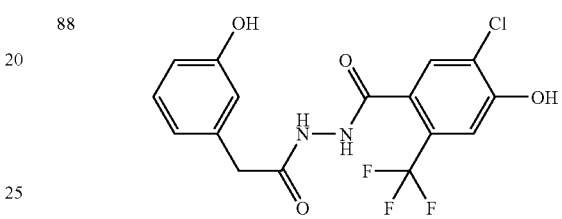 | or pharmaceutically usable salts or stereoisomers thereof, including mixtures thereof in all ratios.

18. Process for the preparation of compounds of the formula I according to claim 1 or pharmaceutically usable salts or stereoisomers thereof, comprising a) reacting a compound of the formula II

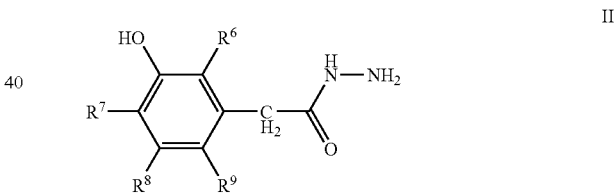

II in which $R^6$, $R^7$, $R^8$ and $R^9$ have the meanings indicated in claim 1, with a compound of the formula III

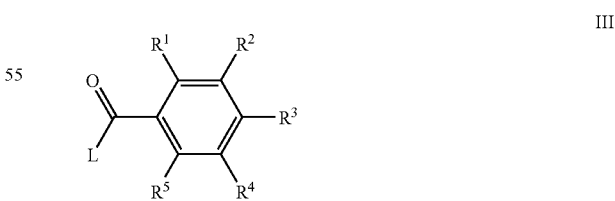

III in which

L denotes Cl, Br, I or a free or reactively functionally modified OH group and $R^1$, $R^2$, $R^3$, $R^4$ and $R^5$ have the meanings indicated in claim 1, or b) reacting a compound of the formula IV

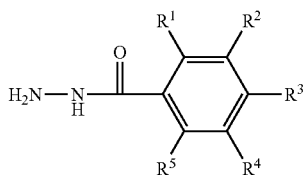

in which
R¹, R², R³, R⁴ and R⁵ have the meanings indicated in claim 1, with a compound of the formula V

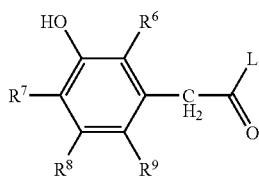

in which
L denotes Cl, Br, I or a free or reactively functionally modified OH group and
R⁶, R⁷, R⁸ and R⁹ have the meanings indicated in claim 1, or c) a radical R¹, R², R³, R⁴, R⁵, R⁶, R⁷, R⁸ and/or R⁹ in a compound of the formula I is converted into another radical R¹, R², R³, R⁴, R⁵, R⁶, R⁷, R⁸ and/or R⁹
by cleaving an ether by hydrolysis or hydrogenolysis,
and/or a base or acid of the formula I is converted into one of its salts.

19. A pharmaceutical composition comprising at least one compound according to claim 1 and/or pharmaceutically usable salt or stereoisomers thereof, including mixtures thereof in all ratios, and pharmaceutically acceptable excipients and/or adjuvants.

20. A method for the treatment of diabetes mellitus, diabetic nephropathy, diabetic neuropathy, diabetic angiopathy and microangiopathy, comprising administering to a host in need thereof a compound according to claim 1 or a salt or stereoisomer thereof, including mixtures thereof in all ratios.

21. A method for the treatment of cardiac fibroses after myocardial infarction, cardiac hypertrophy, cardiac insufficiency and arteriosclerosis, comprising administering to a host in need thereof a compound according to claim 1 or a salt or stereoisomer thereof, including mixtures thereof in all ratios.

22. A method for the treatment of glomerulosclerosis, nephrosclerosis, nephritis, nephropathy or electrolyte excretion disorder, comprising administering to a host in need thereof a compound according to claim 1 or a salt or stereoisomer thereof, including mixtures thereof in all ratios.

23. A method for the treatment of liver cirrhosis, pulmonary fibrosis, fibrosing pancreatitis, rheumatism or arthroses, Crohn's disease, chronic bronchitis, radiation fibrosis, sclerormatitis, cystic fibrosis, scarring and Alzheimer's disease, comprising administering to a host in need thereof a compound according to claim 1 or a salt or stereoisomer thereof, including mixtures thereof in all ratios.

24. A kit consisting of separate packs of
  (a) an effective amount of a compound according to claim 1 and/or pharmaceutically usable salts or stereoisomers thereof, including mixtures thereof in all ratios, and
  (b) an effective amount of a further medicament active ingredient.

25. A method for antibacterial therapy, for increasing learning ability or attention, or for the treatment of cell ageing, stress, or tinnitus in which the inhibition, regulation and/or modulation of kinase signal transduction plays a role, comprising administering to a host in need thereof a compound of claim 1.

* * * * *